(12) United States Patent
Rosin

(10) Patent No.: US 6,862,536 B2
(45) Date of Patent: Mar. 1, 2005

(54) MEASURING SYSTEM AND A METHOD FOR MEASURING PARTICLE VELOCITY AND/OR PARTICLE VELOCITY DISTRIBUTION AND/OR PARTICLE SIZE DISTRIBUTION

(75) Inventor: Tomas Rosin, Turku (FI)

(73) Assignee: TR-Tech Int. Oy, Turku (FI)

( * ) Notice: Subject to any disclaimer, the term of this patent is extended or adjusted under 35 U.S.C. 154(b) by 145 days.

(21) Appl. No.: 10/311,012

(22) PCT Filed: Jul. 3, 2001

(86) PCT No.: PCT/FI01/00635

§ 371 (c)(1),
(2), (4) Date: Dec. 12, 2002

(87) PCT Pub. No.: WO02/06775

PCT Pub. Date: Jan. 24, 2002

(65) Prior Publication Data

US 2003/0163290 A1 Aug. 28, 2003

(51) Int. Cl.⁷ .......................... G06F 19/00; G06F 17/00; G01R 29/12
(52) U.S. Cl. ...................... 702/29; 73/61.75; 73/865.5; 175/66; 356/28; 356/336; 427/180; 427/142; 702/142; 702/190; 324/452; 324/457
(58) Field of Search ................ 702/142, 29, 190; 73/28.02, 61.75, 861.16, 865.5; 324/452, 457; 356/28.5, 28, 336; 175/66; 427/180

(56) References Cited

U.S. PATENT DOCUMENTS

| 3,719,090 | A | * | 3/1973 | Hathaway | 73/865.5 |
| 4,010,366 | A | | 3/1977 | Neukermans et al. | 250/282 |
| 4,401,695 | A | * | 8/1983 | Sopko | 427/180 |
| 4,434,861 | A | * | 3/1984 | Howeth | 175/66 |
| 4,531,402 | A | | 7/1985 | Reif et al. | 73/28.02 |
| 5,059,909 | A | | 10/1991 | O'Brien | 324/457 |
| 5,214,386 | A | | 5/1993 | Singer et al. | 324/452 |
| 5,271,280 | A | | 12/1993 | Nissen | 73/861.16 |
| 5,296,910 | A | | 3/1994 | Cole | 356/28.5 |
| 5,502,658 | A | | 3/1996 | Relin | 702/142 |
| 5,561,515 | A | * | 10/1996 | Hairston et al. | 356/28 |
| 5,831,150 | A | * | 11/1998 | Sowerby et al. | 73/61.75 |
| 6,031,378 | A | * | 2/2000 | Rosin | 324/452 |
| 2001/0035954 | A1 | * | 11/2001 | Rahn et al. | 356/336 |

FOREIGN PATENT DOCUMENTS

| GB | 1 485 750 | 9/1977 |
| GB | 2 063 482 | 6/1981 |
| WO | WO 98/26255 | 6/1998 |

OTHER PUBLICATIONS

Provisional application No. 60/188,278, filed on March 10, 2000.*

* cited by examiner

Primary Examiner—John Barlow
Assistant Examiner—John Le
(74) Attorney, Agent, or Firm—Nixon & Vanderhye P.C.

(57) ABSTRACT

Measuring systems and methods measure particle velocity and/or particle velocity distribution and/or particle size or particle size distribution. The measuring system includes a filter for filtering collected signals which is arranged to pass signals at a relevant frequency band or at relevant frequency bands. The relevant frequency band or frequency bands are arranged to correspond to a frequency band or frequency bands defined by frequencies which exist in consequence of one or more process equipment or a process occurrence affecting to the medium flow.

20 Claims, 1 Drawing Sheet

US 6,862,536 B2

Figure 1:
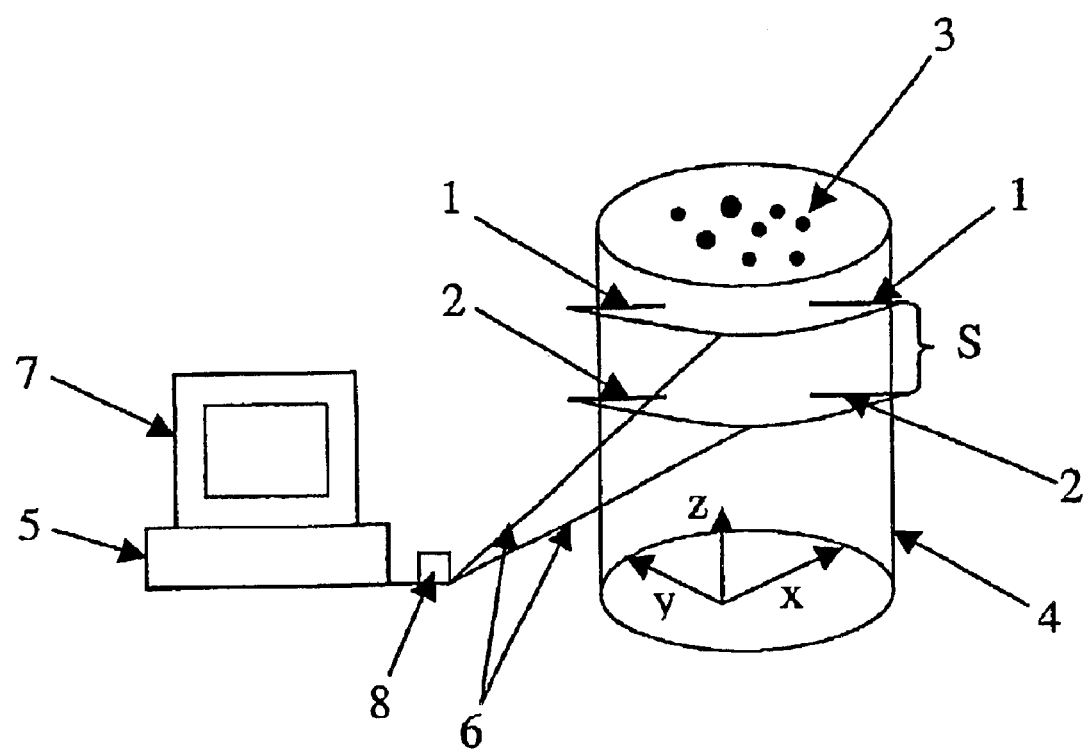

MEASURING SYSTEM AND A METHOD FOR MEASURING PARTICLE VELOCITY AND/OR PARTICLE VELOCITY DISTRIBUTION AND/OR PARTICLE SIZE DISTRIBUTION

CROSS-REFERENCE TO RELATED APPLICATION

This application is the U.S. national phase of international application PCT/FI01/00635 filed 3 Jul. 2001 which designated the U.S.

FIELD OF THE INVENTION

The present invention relates to a measuring system and a method for measuring particle velocity and/or particle velocity distribution and/or particle size and/or particle size distribution as described in more detail in the preamble of the appended independent claims. The invention also relates to computer programs used in the measuring system.

BACKGROUND AND SUMMARY OF THE INVENTION

The above-mentioned measuring system typically comprises at least a sensor comprising at least one sensing element placed in a flow of medium, so that the electric charge of a moving particle induces an electric signal in the sensing element, and means comprising a processor unit with a signal-processing unit connected to the sensor to collect the signals from the sensing element.

One adaptable measuring system has been introduced in the U.S. Pat. No. 6,031,378 whose entire contents are hereby incorporated by reference. When the above measuring system is used for velocity measurements, it comprises at least two sensing elements placed at a known distance from each other in the flow direction of medium, arranged so that the electric charge of a moving particle induces an electric signal in the sensing elements. The velocity measurement is based on detecting a phase angle between the signals of these sensing elements. In addition to motion in the direction of the flow, particles typically exhibit cyclic motion in a direction substantially perpendicular to the flow. Due to a physical distance in the flow direction between these two sensing elements, the cyclic motion causes a phase angle between the signals of these sensing elements. The measuring system comprises means for calculating the phase angle between collected signals and means for calculating the particle velocity according to calculated phase angle.

A device for contactless measurement of a state variable of a flowing medium containing electrically charged particles has been suggested in a patent application WO 98/26255. A two dimensional sensor element is arranged parallel to the particle trajectory or at least two sensor elements, for example electrodes, are arranged in series seen in the flow direction. Charges on these electrodes are influenced by electrically charged particles flying past the electrodes, and voltage signals are produced using suitable amplifiers. A voltage change component is evaluated to determine particle concentration. In order to determine particle velocity, the transit time is evaluated. In order to determine the particle throughput, both the signal strength and the time shift of the individual signals are comparatively evaluated.

Particles do not necessarily follow a straight path in the z direction, direction of the flow (see FIG. 1). The particles also have in addition to the cyclic motion, other sideways motion components in the x and y directions, perpendicular to the flow, due to gas turbulence and collision between themselves. The particle velocity differs from the gas velocity due to a slip between the gas flow and the particle flow. The gas has a higher velocity than the particles. It has been observed that the slip is not constant. The slip depends on the concentration of particles in the gas and, naturally on the particle size. For instance heavy roping of the coal dust in a burner duct leads to an increased local concentration of the particles and therefore to a bigger slip.

The movement of a particle in the flow direction induces a certain, quite slowly varying signal component to a measuring electrode. A cyclic movement of a particle in the direction perpendicular to the flow direction induces an alternating signal component to the measuring electrode. In principle each charged particle thus causes a signal component having a slowly varying part and an alternating part. A signal measured using an electrode is a sum of the signal components relating to various charged particles, and it typically comprises a slowly varying DC—(direct current) part and an AC—(alternating current) part. The DC-part of a measured signal typically originates from the flow (in other words, from the movement of particles in the direction of the flow). The AC part of a measured signal is due to, for example, a cyclic motion of the particles, which motion is perpendicular to the flow direction and is caused by a fan, gas pressure gradients, non-uniform charge distribution of the particles and/or in non-uniform velocity distribution of the particles.

Particles have a fairly strong sideways motion due to gas turbulence and collisions between themselves. This sideways motion will create heavy disturbances to the above mentioned velocity measurement, which uses the cyclic motion. The velocity measurement of this measurement system is disturbed because the signals created on the down and upstream sensors do have a phase angle, which is related to various other factors in addition to the particle velocity along the conduit. Therefore, above measuring system seems to be highly sensitive to interference from these sideway motions.

Another prior art method and apparatus for particle analysis is described in the U.S. Pat. No. 5,296,910. The disclosed method comprises the steps of supplying particles to be tested to a sensing volume of a laser Doppler velocimeter, exciting the particles in the sensing volume with a plurality of forces which are orthogonal over an interval corresponding to a cycle of a fundamental frequency of said forces and which have a zero mean force over said interval, and sensing resulting motion of the particles in the sensing volume to obtain a sensor signal, wherein said sensor signal includes components representative of physical characteristics of the particles. The above method suffers the disadvantage that light-scattering instruments used in the method are vulnerable to get dirty in process conditions raising inaccuracy in the measurement. Further, opaque samples cannot be measured.

A method for measurement of the mass of a charged particle is described in the U.S. Pat. No. 4,010,366. The disclosed method involves ejecting the particle into a sampling device made up of a tube comprising a Faraday cage with a region of a grounded conductive material on either end of it. The particle flows through the tube in a stream of gas and as it passes through the Faraday cage it induces a charge on the cage wall. By measuring the magnitude of the induced charge or its duration in the cage, the magnitude of the charge on the particle or the mass of the particle can be determined. Because this prior art method requires sampling prior to measuring, the method is unsuited to on-line measurement of particle size.

It is an object of the present invention to provide a new, reliable and, as to its design, a simple measuring system and a method for measuring particle velocity and/or particle velocity distribution and/or particle size and/or particle size distribution in e.g. flowing powdery mediums, gas flows, or material webs in various kinds of processes and environments, in order to obtain measuring values which can be used for controlling these processes or which can be used to evaluate their conditions.

It is a particular object of this invention is to provide a measuring system and a method which eliminates the impact of the inherent disturbances on the particle velocity measurement.

Another object of this invention to provide a measuring system and a method which is also suited for use in industrial processes under severe, e.g. dust-laden and/or interference laden conditions.

It is a further object of the invention to use the method in controlling of a burner system or a mill in order to constitute a certain particle velocity and/or particle size and/or a minimum magnitude of fluctuations in the burner system or the mill, or in controlling of particle size or particle velocity e.g. in a grinding circuit or in a transport duct, or in controlling of rate of air flow and fuel flow in a diesel motor.

It is a further object of the invention to provide a measuring system, which does not require calibration before or while measuring particle velocity.

It is a further object of the invention to provide computer programs, which calculates particle velocity and/or particle size from collected signals within relevant frequency band.

The above stated objects are achieved by means of measuring systems, methods, computer programs and uses which are characterized by what have been stated in the characterizing part of the appended independent claims.

A measuring system for measuring properties of particles in a medium flow according to the invention comprises typically means for filtering collected signals arranged to pass signals at a relevant frequency band or at relevant frequency bands so that measurements can be made in a relevant frequency band or frequency bands. In order to carry out measurements calculations are carried out by the signal-processing unit connected to the sensor. The signal-processing unit can be a computer or a device based on a simple microprocessor. The means for filtering collected signals, here also called filter, will then have a filtering effect on the measuring signals, which are conducted from the sensor to the signal-processing unit. Thus, only signals in the relevant frequency band or frequency bands are used in measuring the properties of particles. Filtering of the measuring signals results in the fact, that the measurements will be made on the frequency band or bands of the pressure gradients affecting the particle motion. Interference at known frequencies can, if necessary, be filtered off. A typical example of an external interference, which is preferably filtered off, is the 50/60 Hz frequency of the electrical network.

The relevant frequency band or bands are preferably defined by frequencies which exist in consequence of one or more process equipment or a process occurrence affecting to the medium flow. The relevant frequency band may comprise one or more frequencies and, thus even a single frequency is called as frequency band in this connection.

The medium flow referred to above can be gas flow or fluid flow or a two-phase flow stream including liquid and gas components. The particle can advantageously be powdery particle, pulverous particle, pulverulent particle, granule particle, ionized gas or liquid molecules.

BRIEF DESCRIPTION OF THE ACCOMPANYING DRAWING

The invention will now be described more in detail in the following with reference to the accompanying drawing, in which FIG. 1 shows schematically an embodiment of the measuring system according to the invention.

DETAILED DESCRIPTION OF THE INVENTION

A measuring system according to an embodiment of the invention is schematically illustrated in FIG. 1. The measuring system comprises a sensor comprising two sensing elements 1 and 2 which are placed in the flow of medium 3 in a pipe 4. S indicates distance between the sensing elements and x, y, z indicates different flow directions of the particles. The sensing elements 1 and 2 are connected to a computer 5 via cables 6. Between the sensor and the computer there may be a voltage meter, a capacitor circuit and/or A/D converter as illustrated in applicant's earlier U.S. Pat. No. 6,031,378. A monitor 7 is connected to the computer. The measuring system can also be connected to a central control system, e.g. by way of a computer network.

If the measuring system is used only to measure particle size and/or particle size distribution, there is usually no need to use more than one sensing element in the system.

According to a preferred embodiment of the invention the sensor comprises at least two sensing elements placed at known distance from each other in the flow direction of the medium. The distance between two sensing elements can be about 1–80 millimeters, typically 40–70 millimeters and preferably 45–55 millimeters in the main flow direction. When having short sensing element spacing, the sideways motion of particles, due to gas turbulence and collision, will not cause any error in the velocity reading, thanks to the fact that x and y motion will cause an in-phase signal in both sensors. These in-phase signals can be detected as an error signal, and the impact of the in-phase signals can be removed from the velocity calculations. If the sensor spacing is too long the correlation between the signals of the two sensing elements becomes poor. This will have a negative impact on the velocity measurement result and therefore, the sensing element spacing is preferably limited up to 80 mm.

A sampling rate used in the system is preferably at least 10 times greater than the frequency of the occurrence of the relevancy frequency band and normally the sampling rate is 20 kHz–1 MHz.

In order to detect properties of particles in a medium flow, the collected signals are filtered with filtering means, such as a notch filter 8, so that detection of properties of particles 3 can be made in the relevant frequency band or frequency bands. For example, the collected signals can be filtered in frequency bands 2 Hz and 50 Hz in order to detect properties of particles in relevant frequency bands, which thus do not include the above mentioned frequencies. The used notch filter can be controllable. Filtering could also be carried out by using band bass filter or by utilizing different kinds of spectral filtering methods.

Gas is generally put into motion by a fan with wings and/or by a compressor. The fan or the compressor will generate pressure gradients in the flow, which fall into a certain frequency band, for instance 20–3000 Hz. The frequency band $F_L \ldots F_H$ of the pressure gradients caused by a fan is calculated as follows:

$$F_L = 1*R \text{ (Hz)}$$

$$F_H = N*R \text{ (Hz)}$$

Where R is the speed of revolutions of the fan wheel (rounds per second), N is the number of the fan wings and L represents the lower limit and H, consequently the higher limit. Typically R is not constant, but varies within certain limits.

Thus the relevant frequency band for the velocity measurements is preferably defined by the fans causing the movement of the medium flow, so that a lower limiting frequency of the relevant frequency band is related to the minimum speed of revolutions of the fan and the upper frequency limit of the relevant frequency band is related to the maximum speed of revolutions of the fans multiplied with number of the wings of the fans.

The desired frequency band can be defined also by frequencies which exist in the medium flow in consequence of other process equipments and process occurrences affecting to the medium flow. Above process occurrences could be for example chemical reactions and chemical changes.

The measuring system can include means for detecting and characterizing the relevant frequency bands that are present because of process equipment such as fans and feeders or process occurrences before filtering. These detected and characterized frequency bands are used for filtering the signals from the sensor. Some preliminary parameters can be input to the measuring system to aid in detection and characterization. The preliminary parameters can include, for example, number of fans or compressors in the system, operation speeds of the fans and etc. The means referred to above comprises sophisticated computer programs and different kinds of signal analyzers.

The periodic pressure gradients in the medium will affect the particle motion and create a corresponding periodic signal on the frequency bands in the sensing elements of the pressure gradients. As the particles have a motion in the flow direction the periodic signal will cause a phase angle between the signal obtained from the two sensing elements. The phase angle depends on the particle flow velocity: the longer a particle remains between the sensing elements, the larger the phase angle will be. Hence, the measuring system according to the invention can be used to detect the particle velocities. In the method the signals from the upstream sensing elements 2 and downstream sensing elements 1 are collected. The collected signals are filtered and the phase angle between the collected signals for the relevant characterized frequency bands is calculated. The particle velocity is calculated according to the calculated phase angle. Filtering the collected signals removes effect of disturbances caused by sideways motion and leaves the periodic signal originating from periodic pressure gradients and cyclic particle motion.

The velocity calculation can be corrected by detecting in-phase and other disturbing signals between upstream and downstream sensing elements and removing the impact of the signals having a negative impact on the measurement result, from the velocity calculation.

Big particles behave differently than small particles in a gas stream. The drag force $F_d$ acting on the particle is calculated as follows:

$$F_d=0.5*Cd*A*\rho*W^2,$$

where A is the projection area of the particle, ρ is the density of the gas and W is the velocity difference between the gas and the particle. It should be stressed that the specific area (area/weight) $A_s$ of particle increases along with decreasing particle size. Hence a big particle has a bigger mass in relation to its area than a smaller one has. This fact will lead to that, that a small particle reacts more to fast changes in gas velocity than a big one.

When particles are entrained in the gas stream they are accelerated to a certain speed. This requires energy, which is gained from the kinetic energy of the gas stream. The more particles that entrain into the gas stream, the more the velocity of the suspension will decrease, assuming that the fan power, keeping up the flow, is kept constant.

Pressure gradients in the gas flow will also have an impact on the motion of the particles. That is, the particles will accelerate and retardate in phase with these cyclic pressure gradients. The acceleration of big particles will decrease much more with increased pressure gradient frequency than the acceleration for small particles will decrease.

Therefore, by calculating the phase angle for several frequency lines within the relevant frequency band or bands a velocity distribution can be calculated from the phase angle of the different spectral lines.

The big particles are affected more by cyclic pressure gradients on lower frequencies than on higher frequencies due to their higher momentum. Therefore, by identifying the spectrum, on the frequency band $F_L<f<F_H$, of the measured voltage variation the particle size distribution can be estimated. By identifying certain patterns and comparing the spectral density in the low band (example 26–126 Hz) with the density in the high band (example 126–260 Hz) the particle size distribution can be estimated.

By calculating accurate spectra of the collected signals and comparing the spectra referred to above to one or more comparison spectra the particle size can be estimated using the measuring system according to the invention. The comparison spectra data can be collected from previous measurements or it can be supplied by an exterior source such as from laboratory measurements.

An external source that produces sound, creating pressure gradients, can be implemented to put the particles and/or ions in cyclic motion. The frequencies and magnitude of the sound can then be manipulated to create the most favorable cyclic motion of the particles.

An external source for creating ions or electrical charges in a gas on a certain frequency band, preferably 1–10 Hz, is implemented in such a manner that it is able to measure the velocity of a gas, which inherently is not charged with static electricity. The above ionization is typically adopted to the frequencies which exist in the gas due to process equipments and process occurrences affecting to the gas flow.

The measuring system and the measuring method may advantageously be used e.g. for controlling the supply of additives in a process, controlling the reaction time of a process, controlling the degree of grinding of the starting material in a process, controlling the supply of heat to a process and/or for controlling a combustion process.

The measuring system and the measuring method may advantageously be used also in controlling of a burner system or a mill in order to constitute a certain particle velocity and/or particle size and/or a minimum magnitude of fluctuations in the burner system or in the mill. They may be used also in controlling of particle velocity and/or particle size in a grinding circuit or in controlling of particle velocity in a transport duct. They may also be used in controlling of rate of air flow and fuel flow in a motor, e.g. in a diesel motor.

As indicated above, aspects of this invention pertain to specific "method functions" implementable on computer systems. In an alternate embodiment, the invention may be implemented as a computer program and as a computer program product for use with a computer system. Those skilled in the art should readily appreciate that programs defining the functions of the present invention can be delivered to a computer in many forms; including, but not limited to: (a) information permanently stored on non-writable storage media (e.g. read only memory devices within a computer such as ROM or CD-ROM disks readable by a computer I/O attachment); (b) information alterably stored on writable storage media (e.g. floppy disks and hard drives); or (c) information conveyed to a computer through communication media such as network and telephone networks via modem. It should be understood, therefore, that such media, when carrying computer readable instructions that direct the method functions of the present invention, represent alternate embodiments of the present invention.

One such embodiment is drawn to a computer program product comprising: a computer usable medium having computer readable program code and computer readable system code embodied on said medium for collecting signals from a sensor and calculating the phase angle between the collected signals and to calculate the particle velocity according to the calculated phase angle.

The computer program product can further include computer readable program code means for detecting in-phase signals between upstream and downstream sensing element and to remove the impact of the impact of the in-phase signals from the velocity calculation.

Another embodiment of the invention embodied on a computer program product comprising: computer readable program code means for collecting signals from a sensor, and computer program code means adapted to calculate the spectrum of the collected signals within the relevant frequency band or bands and to evaluate the particle size from the spectrum.

The invention is not limited to the embodiments described and illustrated above, but can be varied in many ways within the scope and spirit of the invention, which is defined in the appended claims.

What is claimed is:

1. A measuring system for measuring properties of particles in a medium flow, said measuring system comprising:

a sensor comprising at least one sensing element placed in the flow of medium, so that an electric charge of a moving particle induces an electric signal in the sensing element, and a processing unit with a signal-processing unit connected to the sensor to collect the signals from the sensing element, wherein the measuring system comprises filtering means for filtering collected signals, said filtering means arranged to pass signals at a relevant frequency band or at relevant frequency bands, said filtering means being connected to said signal-processing unit for feeding said passed signals to the signal-processing unit, wherein the relevant frequency band or frequency bands are arranged to correspond to a frequency band or frequency bands defined by frequencies which exist in consequence of one or more process equipment or a process occurrence affecting to the medium flow, and wherein said filtering means is arranged to pass signals at the relevant frequency band or bands corresponding to a frequency band or frequency bands defined by fans causing the movement of the medium flow, so that at least one frequency band defined by one fan is defined so that a lower limiting frequency of the frequency band is related to a minimum revolution speed of the fan, and so that an upper frequency limit of the frequency band is related to a maximum revolution speed of the fans multiplied with number of wings of the fans.

2. A measuring system according to claim 1, further comprising detecting and characterizing means for detecting and characterizing frequency bands caused by process equipment, and means for setting the relevant frequency bands for filtering means corresponding to the characterized frequency bands, wherein said filtering means pass signals.

3. A measuring system as claimed in claim 2, wherein the process equipment is selected from fans, feeders, ionisators or sound generators.

4. A method for detecting properties of particles in a medium flow comprising utilizing a measuring system including a sensor comprising at least one sensing element placed in the flow of medium, so that an electric charge of a moving particle induces an electric signal in the sensing element, filtering means arranged to pass the signals at least at one or more relevant frequency bands, and a processing unit with a signal-processing unit connected to the sensor to collect the signals from the sensing element in order to detect particle properties in the relevant frequency band or bands, wherein the relevant frequency band or bands are defined by frequencies which exist in consequence of one or more process equipment or a process occurrence affecting to the medium flow, said frequency band or bands are defined by fans causing the movement of the medium flow, so that at least one relevant frequency band defined by one fan is defined so that the lower limiting frequency of the frequency band is related to a minimum revolution speed of the fan and an upper frequency limit of the frequency band is related to a maximum revolution speed of the fans multiplied with the number of wings of the fans.

5. A method according to claim 4, wherein the frequency bands caused by process equipment detected and characterized before filtering, and wherein the frequency bands are used in filtering the signals from the sensor.

6. A method according to claim 4, wherein particle velocity is detected utilizing a measuring system, which comprises at least two sensing elements placed at a known distance from each other in the flow direction of medium and collecting the signals from upstream and downstream sensing elements and calculating the phase angle between the collected signals within the relevant frequency band or bands and calculating the particle velocity according to the calculated phase angle.

7. A method according to claim 6, comprising detecting in-phase signals between upstream and downstream sensing elements and removing the impact of the in-phase signals from the velocity calculation.

8. A method according to claim 6, comprising calculating the phase angle between the signals for different frequency lines within said relevant frequency bands and calculating the velocity for the said frequency lines.

9. A method according to claim 6, wherein the calculated velocities for different frequency lines are used to calculate particle velocity distribution.

10. A method according to claim 4, comprising calculating accurate spectra of the collected signals and evaluating the spectra on said at least one relevant frequency band by comparing the spectral density in the low-band with the density in the high band to determine the particle size distribution.

11. A method according to claim 4, comprising calculating accurate spectra of the collected signals and determining the particle size by comparing said spectra to one or more comparison spectra.

12. A use of the method according to claim 4 in controlling of a burner system or a mill in order to constitute a certain particle velocity and/or particle size and/or a minimum magnitude of fluctuations in the burner system or the mill.

13. A use of the method according to claim 4 in controlling of particle velocity and/or particle size in a grinding circuit.

14. A use of the method according to claim 4 in controlling of particle velocity in a transport duct.

15. A use of the method according to claim 4 in controlling of rate of air flow and fuel flow in a diesel motor.

16. A computer program comprising:

computer program code means adapted to collect signals from a sensor, and computer program code means adapted to calculate the phase angle between the collected signals within the relevant frequency band or bands corresponding to a frequency band or frequency bands defined by fans causing the movement of the medium flow, so that at least one frequency band defined by one fan is defined so that a lower limiting frequency of the frequency band is related to a minimum revolution speed of the fan and an upper frequency limit of the frequency band is related to a maximum revolution speed of the fans multiplied by the number of the wings of the fans, and to calculate the particle velocity according to the calculated phase angle.

17. A computer program according to claim 16 comprising computer program code means adapted to detect in-phase signals between upstream and downstream sensing element and to remove the impact of the in-phase signals from the velocity calculation.

18. A computer program as claimed in claim 16 embodied on a computer readable medium.

19. A computer program comprising:

computer program code means adapted to collect signals from a sensor, and computer program code means adapted to calculate the spectrum of the collected signals within the relevant frequency band or bands corresponding to a frequency band or frequency bands defined by fans causing the movement of the medium flow, so that at least one frequency band defined by one fan is defined so that a lower limiting frequency of the frequency band is related to a minimum revolution speed of the fan and an upper frequency limit of the frequency band is related to a maximum revolution speed of the fans multiplied by the number of wings of the fans and to evaluate the particle size from the spectrum.

20. A computer program as claimed in claim 19 embodied on a computer readable medium.

* * * * *

UNITED STATES PATENT AND TRADEMARK OFFICE
CERTIFICATE OF CORRECTION

PATENT NO.    : 6,862,536 B2
DATED         : March 1, 2005
INVENTOR(S)   : Thomas Rosin Page 1 of 1

It is certified that error appears in the above-identified patent and that said Letters Patent is hereby corrected as shown below:

<u>Title page,</u>
Item [30], Foreign Priority Data, should read
-- FI20001685   July 19, 2000 --

Signed and Sealed this

Twenty-fourth Day of May, 2005

JON W. DUDAS
*Director of the United States Patent and Trademark Office*